(12) United States Patent
Blood et al.

(10) Patent No.: US 10,870,009 B2
(45) Date of Patent: Dec. 22, 2020

(54) BUZZER APPARATUS

(71) Applicant: Cardiac Pacemakers, Inc., St. Paul, MN (US)

(72) Inventors: James E. Blood, Shoreview, MN (US); Scott A. Spadgenske, Buffalo, MN (US); Doug E. Giwoyna, Harris, MN (US); Lonnie D. Myers, Lindstrom, MN (US); Shawn Larson, Minneapolis, MN (US); David A. Chizek, Brooklyn Park, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 292 days.

(21) Appl. No.: 15/862,118

(22) Filed: Jan. 4, 2018

(65) Prior Publication Data
US 2018/0185658 A1 Jul. 5, 2018

Related U.S. Application Data

(60) Provisional application No. 62/442,286, filed on Jan. 4, 2017.

(51) Int. Cl.
| | | |
|---|---|---|
| *A61N 1/37* | (2006.01) | |
| *A61N 1/372* | (2006.01) | |
| *A61N 1/362* | (2006.01) | |
| *A61N 1/39* | (2006.01) | |
| *A61N 1/08* | (2006.01) | |

(52) U.S. Cl.
CPC ......... *A61N 1/37258* (2013.01); *A61N 1/08* (2013.01); *A61N 1/3627* (2013.01); *A61N 1/3956* (2013.01)

(58) Field of Classification Search
CPC .... A61N 1/08; A61N 1/3627; A61N 1/37258; A61N 1/3956; G10K 9/122; H01L 41/0475; H01L 41/0533; H01L 41/29; H05K 1/09; H05K 1/115; H05K 1/183; H05K 1/185; H05K 1/189; H05K 2201/10083; H05K 2203/0307; H05K 2203/072; H05K 2203/107; H05K 2203/1469; H05K 3/0026; H05K 3/422
See application file for complete search history.

(56) References Cited

U.S. PATENT DOCUMENTS

| | | |
|---|---|---|
| 4,612,934 A | 9/1986 | Borkan |
| 5,313,953 A | 5/1994 | Yomtov et al. |
| 5,944,746 A | 8/1999 | Kroll |

(Continued)

OTHER PUBLICATIONS

"Flexible Microcircuits for RF/microwave and Medical Biosensor Applications", Metrigraphics, http://www.metrigraphicsllc.com/, Oct. 5, 2016, 3 pgs.

*Primary Examiner* — Amanda K Hulbert
(74) *Attorney, Agent, or Firm* — Schwegman Lundberg & Woessner, P.A

(57) ABSTRACT

This document discusses, among other things, systems and methods related to a flexible circuit buzzer apparatus, such as a buzzer apparatus for use in an implantable medical device. In an example, the buzzer apparatus can include a flexible circuit having a first dielectric layer. A conductive layer can be disposed on the first dielectric layer. A hole can be formed in the first dielectric layer, the conductive layer, or both. A buzzer including a first contact can be located proximate to the hole. A conductive via can be plated or deposited in the hole. At least the first contact can be electrically coupled to the conductive layer by the conductive via.

14 Claims, 8 Drawing Sheets

(56) References Cited

U.S. PATENT DOCUMENTS

| | | |
|---|---|---|
| 6,521,530 B2 | 2/2003 | Peters et al. |
| 6,920,359 B2 | 7/2005 | Meadows et al. |
| 7,068,491 B1 | 6/2006 | Burdon et al. |
| 7,865,244 B2 | 1/2011 | Giftakis et al. |
| 8,184,833 B2 | 5/2012 | Demuynck |
| 8,269,634 B2 | 9/2012 | Fischell et al. |
| 8,313,831 B2 | 11/2012 | Tanaka et al. |
| 9,148,728 B2 | 9/2015 | Polster et al. |
| 2010/0103634 A1 | 4/2010 | Funaya et al. |
| 2014/0048906 A1 | 2/2014 | Shim et al. |
| 2015/0343226 A1 | 12/2015 | Barbagelata et al. |

BUZZER APPARATUS

CLAIM OF PRIORITY

This application claims the benefit of priority under 35 U.S.C. § 119(e) of U.S. Provisional Patent Application Ser. No. 62/442,286, filed on Jan. 4, 2017, which is herein incorporated by reference in its entirety.

TECHNICAL FIELD

This document relates generally to medical devices, and more particularly, but not by way of limitation, to systems, devices, and methods to electrically couple a buzzer to a flexible circuit laminate.

BACKGROUND

Speaker assemblies, such as speakers in medical devices are often soldered to an electrical circuit. In some examples, the speaker can be soldered to one or more wires or one or more traces of an electrical circuit. Flexible circuits are sometimes fabricated with alternating layers of polymer dielectric and metallic conductor bonded together with adhesive. Heat from the soldering process can damage a flexible circuit. For instance, excessive temperature or time of exposure to the heat source can melt the dielectric. Solder can also leave flux and other contaminants on the flexible circuit. Contaminants can reduce adhesion between layers of a flexible circuit lamination. Sometimes a cleaning step is required to remove the contaminants before additional assembly steps can proceed adding extra cost and time for fabrication. Furthermore, the solder joint may not be level with a surrounding surface of the flexible circuit laminate. For instance, the solder joint may be sunken or raised with respect to the surrounding solder pad or copper trace. Uneven surfaces can result in lamination difficulties or delamination issues following assembly.

SUMMARY

This document discusses, among other things, systems and methods to electrically couple a speaker or other audio device (e.g., buzzer) to circuitry of an implantable medical device, such as a pacemaker (e.g. implantable cardioverter defibrillator (ICD) or cardiac resynchronization therapy device (CRT)).

Example 1 is an implantable medical device comprising: a housing; a controller circuit in the housing; a flexible circuit buzzer apparatus in the housing, the buzzer apparatus including: a flexible circuit, a buzzer laminated into the flexible circuit, a conductive via in the flexible circuit; and wherein the buzzer is operatively coupled to the controller circuit through the via.

In Example 2, the subject matter of Example 1 optionally includes wherein the flexible circuit includes a first dielectric layer including a first hole extending through the first dielectric layer, a first conductive layer disposed on the first dielectric layer, the buzzer includes a first contact located proximate to the first hole; and the conductive via in the first hole, the first contact being electrically coupled to the first conductive layer by the conductive via, and the first conductive layer being coupled to the controller circuit.

In Example 3, the subject matter of any one or more of Examples 1-2 optionally includes a second dielectric layer, the buzzer being between the first dielectric layer and the second dielectric layer, wherein the buzzer is electrically isolated from a surrounding environment.

In Example 4, the subject matter of any one or more of Examples 1-3 optionally includes wherein the flexible circuit further includes a second hole extending through the first dielectric layer, and a second conductive via in the second hole, the second conductive via being electrically coupled to the first conductive layer.

In Example 5, the subject matter of any one or more of Examples 1-4 optionally includes wherein the flexible circuit further includes a third hole extending through the first dielectric layer, and a third conductive via in the third hole, the third conductive via being coupled to a ground connection.

Example 6 is a method of forming a laminated flexible circuit buzzer apparatus for use in an implantable medical device, comprising: forming a hole into a first dielectric layer, the hole including a first opening and a second opening, wherein the first opening is located adjacent to a first contact of a buzzer, wherein the first dielectric layer includes a first conductive layer; and plating the hole and the first contact to form a conductive via, the conductive via electrically coupling the first conductive layer to the first contact.

In Example 7, the subject matter of Example 6 optionally includes wherein forming the hole includes laser drilling the hole into the first dielectric layer.

In Example 8, the subject matter of any one or more of Examples 6-7 optionally includes 150 µm or less transverse to a longitudinal axis of the hole.

In Example 9, the subject matter of any one or more of Examples 6-8 optionally includes producing a surface texture on the first contact of the buzzer by laser drilling, and wherein plating the hole further includes plating the conductive via into the surface texture of the first contact to mechanically couple the first conductive layer to the first contact.

In Example 10, the subject matter of any one or more of Examples 6-9 optionally includes wherein plating the hole and the first contact includes at least one of an electroplating, vapor depositing, chemically depositing, and sputtering process.

In Example 11, the subject matter of any one or more of Examples 6-10 optionally includes wherein plating the conductive via includes plating the conductive via by electroless copper deposition into the hole.

In Example 12, the subject matter of any one or more of Examples 6-11 optionally includes depositing a thin film of copper in the hole and on the first contact when the buzzer is in situ prior to the plating to form the conductive via.

In Example 13, the subject matter of any one or more of Examples 6-12 optionally includes wherein plating the conductive via includes forming a substantially planar surface along the conductive layer and over the second opening.

In Example 14, the subject matter of any one or more of Examples 6-13 optionally includes drilling a group of holes in the dielectric layer, the group of holes proximate to the first contact, and plating the group of holes and the first contact to form a group of conductive vias electrically coupling the first conductive layer to the first contact.

In Example 15, the subject matter of any one or more of Examples 6-14 optionally includes filling a cavity of the conductive via.

Example 16 is a flexible circuit buzzer apparatus for use in an implantable medical device, comprising: a flexible circuit having a first dielectric layer; a conductive layer disposed on the first dielectric layer; a hole in the first dielectric layer; a buzzer including a first contact located proximate to the hole; and a conductive via in the hole, wherein at least the first contact is electrically coupled to the conductive layer by the conductive via.

In Example 17, the subject matter of Example 16 optionally includes wherein the buzzer is located within an aperture of a second dielectric layer, the second dielectric layer is coupled to the first dielectric layer.

In Example 18, the subject matter of any one or more of Examples 16-17 optionally includes a group of redundant conductive vias electrically coupled between the conductive layer and the first contact, a spacing between two or more conductive vias of the group being less than 0.40 mm.

In Example 19, the subject matter of any one or more of Examples 16-18 optionally includes wherein the conductive via is a high density interconnect via having a dimension of 150 μm or less transverse to a longitudinal axis of the hole.

In Example 20, the subject matter of any one or more of Examples 16-19 optionally includes wherein the conductive via includes a plated material selected from at least one of a group comprising a chemically deposited, electroplated, electroless deposition, vapor deposited, evaporative deposited, and sputtered plating.

In Example 21, the subject matter of any one or more of Examples 16-20 optionally includes wherein the conductive via includes electroless copper, electro-deposited copper, or shadow graphite.

In Example 22, the subject matter of any one or more of Examples 16-21 optionally includes wherein the hole includes a first opening on a first side of the first dielectric layer and a second opening on a second side of the dielectric layer, the first opening being proximate the first contact and the second opening being proximate the conductive layer, and wherein the conductive via is tapered, the conductive via having a smaller dimension proximate to the first opening than proximate to the second opening.

Example 23 is a method of forming a laminated flexible circuit buzzer apparatus for use in an implantable medical device, comprising: forming a hole into a first dielectric layer, the hole including a first opening and a second opening, wherein the first opening is located adjacent to a first contact of a buzzer, wherein the first dielectric layer includes a first conductive layer; and plating the hole and the first contact to form a conductive via, the conductive via electrically coupling the first conductive layer to the first contact.

In Example 24, the subject matter of Example 23 optionally includes wherein forming the hole includes laser drilling the hole into the first dielectric layer, the hole having a dimension of 150 μm or less transverse to a longitudinal axis of the hole.

In Example 25, the subject matter of Example 24 optionally includes producing a surface texture on the first contact of the buzzer by laser drilling, and wherein plating the hole further includes plating the conductive via into the surface texture of the first contact to mechanically couple the first conductive layer to the first contact.

In Example 26, the subject matter of any one or more of Examples 23-25 optionally includes wherein plating the hole and the first contact includes at least one of an electroplating, vapor depositing, chemically depositing, and sputtering process.

In Example 27, the subject matter of any one or more of Examples 23-26 optionally includes wherein plating the conductive via includes plating the conductive via by electroless copper deposition into the hole.

In Example 28, the subject matter of any one or more of Examples 23-27 optionally includes wherein plating the conductive via includes filling the hole with shadow graphite.

In Example 29, the subject matter of any one or more of Examples 23-28 optionally includes depositing a thin film of copper in the hole and on the first contact when the buzzer is in situ prior to the plating to form the conductive via.

Example 30 is an implantable medical device comprising: a housing; a controller circuit in the housing; a flexible circuit buzzer apparatus in the housing, the buzzer apparatus including: a flexible circuit, a buzzer laminated into the flexible circuit, a conductive via in the flexible circuit; and wherein the buzzer is operatively coupled to the controller circuit through the via.

In Example 31, the subject matter of Example 30 optionally includes wherein the flexible circuit includes a first dielectric layer including a first hole extending through the first dielectric layer, a first conductive layer disposed on the first dielectric layer, a buzzer including a first contact located proximate to the first hole; and the conductive via in the first hole, the first contact being electrically coupled to the first conductive layer by the conductive via, and the first conductive layer being coupled to the controller circuit.

In Example 32, the subject matter of Example 31 optionally includes a second dielectric layer, the buzzer being between the first dielectric layer and the second dielectric layer, wherein the buzzer is electrically isolated from a surrounding environment.

In Example 33, the subject matter of any one or more of Examples 31-32 optionally includes wherein the flexible circuit further includes a second hole extending through the first dielectric layer, and a second conductive via in the second hole, the second conductive via being electrically coupled to the first conductive layer.

In Example 34, the subject matter of Example 33 optionally includes wherein the flexible circuit further includes a third hole extending through the first dielectric layer, and a third conductive via in the third hole, the third conductive via being coupled to a ground connection.

In Example 35, the subject matter of any one or more of Examples 31-34 optionally includes wherein the buzzer has a central region and a peripheral region, and the first via is located at a peripheral region of the buzzer.

This summary is intended to provide an overview of subject matter of the present patent application. It is not intended to provide an exclusive or exhaustive explanation of the disclosure. The detailed description is included to provide further information about the present patent application. Other aspects of the disclosure will be apparent to persons skilled in the art upon reading and understanding the following detailed description and viewing the drawings that form a part thereof, each of which are not to be taken in a limiting sense.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1:
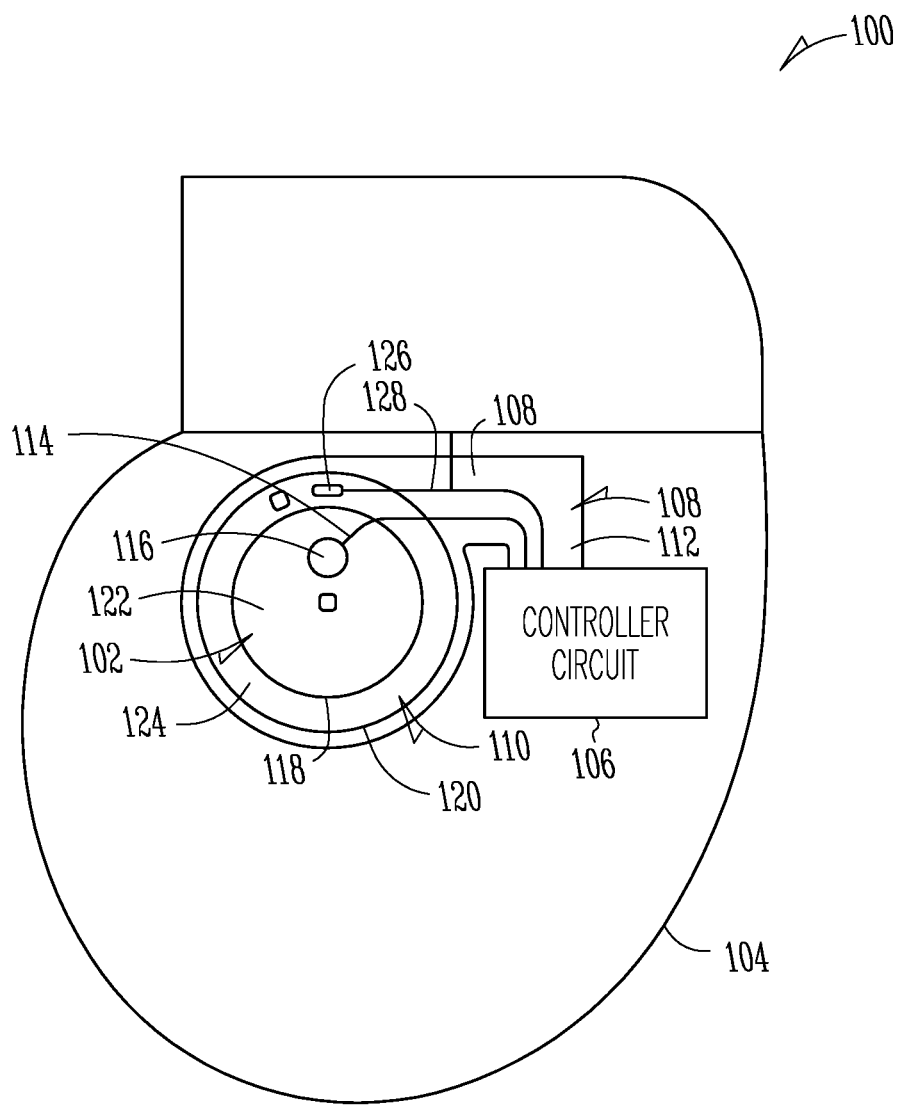
FIG. 1 illustrates a top view of an example of an implantable medical device including a flexible circuit buzzer apparatus, according to an embodiment.

Implantable medical devices, such as a pacemaker (e.g. implantable cardioverter defibrillator (ICD) or cardiac resynchronization therapy device (CRT)), can include a speaker or other audio device. The speaker or audio device can provide a notification to a patient, physician, or other individual. Some speakers, such as a speaker including an electro-magnetic core, can be damaged when subjected to a magnetic field, for instance, from a magnetic resonance imaging (MRI) scan. Because patients having the implantable medical device may be subjected to MRI scans for diagnosis, a piezo electric buzzer (referred to herein as a buzzer) can be used in place of the speaker. The piezo electric buzzer can withstand the magnetic field of MRI scans without permanent damage. Accordingly, the buzzer can provide the notification to the patient, such as an audible notification to indicate low battery, component failure, delivery of therapy, or the like, with less concern for compromised performance after exposure to an MRI scan.

The buzzer can be operatively coupled within the implantable medical device. For instance, the buzzer can be electrically coupled to circuitry of the implantable medical device (device circuitry) by one or more wires or a flexible circuit within the implantable medical device. In an example, the buzzer can be laminated within the flexible circuit to insulate the buzzer, and the circuitry, from a housing of the implantable medical device. For instance, the flexible circuit can include a first dielectric layer disposed on a second dielectric layer. The buzzer can be positioned within an aperture of the second dielectric layer. In an example, the second dielectric layer can be a core of the flexible circuit. A third dielectric layer can be laminated on a side of the second dielectric layer opposing the first dielectric layer to fully encapsulate the buzzer within the flexible circuit.

During the lamination process, the buzzer can be soldered to the flexible circuit. For instance, the first dielectric layer can include a thru-hole. A conductive layer (e.g., trace or solder pad) can be adjacent to or surrounding the thru-hole. One or more contacts of the buzzer can be aligned with the thru-hole. A solder or brazing joint can be formed within the thru-hole by a technician with a soldering iron or by using solder paste in a reflow process to electrically couple the buzzer to the conductive layer of the flexible circuit. Soldering or brazing can be expensive and time consuming during the assembly process, especially if soldering is not otherwise needed at that step of the assembly. After soldering is complete, a further dielectric layer, such as a fourth dielectric layer can be disposed on the first dielectric layer to insulate the joint. However, before the fourth dielectric layer can be applied over the joint (e.g., solder or brazing joint), the first dielectric layer (including the conductive layer thereon and the joint) may need to be cleaned of any remaining flux or other contaminants remaining from the soldering or brazing process. Cleaning can add further cost and time to the assembly process as well as introduce further manufacturing errors. In addition, the high temperature required for soldering or brazing can damage the flexible circuit or the buzzer.

The present inventors have recognized, among other things, that electrically coupling a buzzer to a conductive layer of a flexible circuit with a conductive via can reduce cost, assembly time, and manufacturing defects during assembly of a flexible circuit buzzer apparatus. For instance, in some examples, the flexible circuit buzzer apparatus can be used in an implantable medical device. The flexible circuit can include a first dielectric layer. A conductive layer can be disposed on the first dielectric layer, and a hole can be formed through the first dielectric layer and the conductive layer. The buzzer can include a first contact located proximate to the hole. The first electrical contact can be electrically coupled to the conductive layer by the conductive via located within the hole. In an example, the conductive via can be a high density interconnect via having a dimension of 150 µm or less (as measured transverse to a longitudinal axis of the hole). The conductive via can include a plated material, such as a chemically deposited, electroplated, electroless deposition, vapor deposited, evaporative deposited, sputtered plating, or the like. In various examples, the plated material can include electroless copper, electro-deposited copper, shadow graphite, or other plated or solderless material. The conductive via can be formed to electrically couple the buzzer to the first conductive layer at the same process step of forming other vias in the flexible circuit assembly. For instance, the conductive via and other vias can be plated on the same buildup layer during the flexible circuit lamination process. Thus, the costly, time consuming, or error prone steps, such as soldering, can be avoided. Furthermore, the next buildup layer (or cover layer) can be applied based on standard lamination steps. Accordingly, no additional cleaning step is needed following the formation of the conductive via to electrically couple the buzzer to the flexible circuit. In an example, the apparatus can include a group of redundant conductive vias electrically coupled between the conductive layer and the first contact to increase the robustness of the electrical coupling. To reduce any vibration dampening effect of the group of conductive vias on the buzzer, a spacing between two or more conductive vias of the group can be less than 0.40 mm.

FIG. 1 illustrates a top view of an example of an implantable medical device 100 (referred to herein as a medical device) including a flexible circuit buzzer apparatus 102 (referred to herein as a buzzer apparatus), according to an embodiment. As shown in the example of FIG. 1, the medical device 100 can include, but is not limited to, a pacemaker, an implantable cardioverter defibrillator (ICD), cardiac resynchronization therapy (CRT) device, or other implantable medical device. In an example, the medical device 100 can include a housing 104 that can package a controller circuit 106 and the buzzer apparatus 102. In further examples, the medical device 100 can include a battery, a pulse generator, one or more leads, a wireless transceiver, or other components. Because the medical device 100 can be implanted into a patient, the housing 102 can be constructed of a biocompatible material, such as stainless steel, titanium, or the like. Accordingly, one or more components of the medical device 100, such as the buzzer apparatus 102 can be insulated from the housing 104 to mitigate electrical shorting.

The buzzer apparatus 102 can include a flexible circuit 108 and a buzzer 110. The buzzer 110 can be laminated into the flexible circuit 108. For instance, the flexible circuit 108 can include at least one dielectric layer, such as dielectric layer 112, and at least one conductive layer, such as conductive layer 114, disposed on the dielectric layer 112. The buzzer 110 can be located between two or more dielectric layers (e.g., dielectric layer 112) thereby insulating the buzzer 110 from the housing 104 or other components of the medical device 100. The conductive layer 114 can be constructed of a conductive material, such as copper, tin, sliver, or the like. As shown in the example of FIG. 1, the conductive layer 114 can be patterned to form electrical circuit routing, such as a trace. The conductive layer 114 can be electrically coupled to the buzzer 110 by a conductive via, such as a conductive via 116.

The buzzer 110 can include a piezo electric buzzer. For instance, the piezo electric buzzer can produce vibrations or audible sound waves in response to the application of an electric signal (e.g., having an alternating electric field). In an example, the buzzer 110 can include a central region 118 and a peripheral region 120. The central region 118 can include a piezo electric material and the peripheral region 120 can include a speaker element. The speaker element, such as a metallic diaphragm, can amplify oscillations produced by the piezo electric material and thereby magnify the sound generated by the buzzer 110. A first contact 122 can be located on the central region 118 (e.g., the piezo electric element) of the buzzer 110. A second contact 124 can be located on the peripheral region 120 (e.g., the speaker element) of the buzzer 110. The first contact 122 and the second contact 124 can include a conductive pad, such as a copper, beryllium copper, stainless steel, phosphor bronze, or other conductive pad to facilitate electrical coupling between the operative portions of the buzzer 110 and one or more conductive layers, such as conductive layer 114.

The conductive via, such as the conductive via 116, can be electrically coupled between the first contact 122 and the first conductive layer 114. In the example of FIG. 1, the buzzer apparatus 102 can include a second conductive via, such as conductive via 126, electrically coupled between the second contact 124 and a second conductive layer 128. The controller circuit 106 can be electrically coupled to the first conductive layer 114, the second conductive layer 128, or both. Accordingly, the buzzer apparatus 102 can be operatively coupled (e.g., electrically coupled) to the controller circuit 106 through the first conductive via 116 or the second conductive via 126.

The controller circuit 106 can transmit a signal to the buzzer 110 to produce a vibration or sound from the buzzer 110. For instance, controller circuit 106 can transmit the signal to the buzzer 110 to provide a notification to a patient, such as an audible notification to indicate low battery, component failure, delivery of therapy, or the like. In various examples, the controller circuit 106 can include, but is not limited to, a processor, microcontroller (MCU), system-on-chip (SOC), application specific integrated circuit (ASIC), pulse generator, field programmable gate array (FPGA), or the like.

Figure 2:
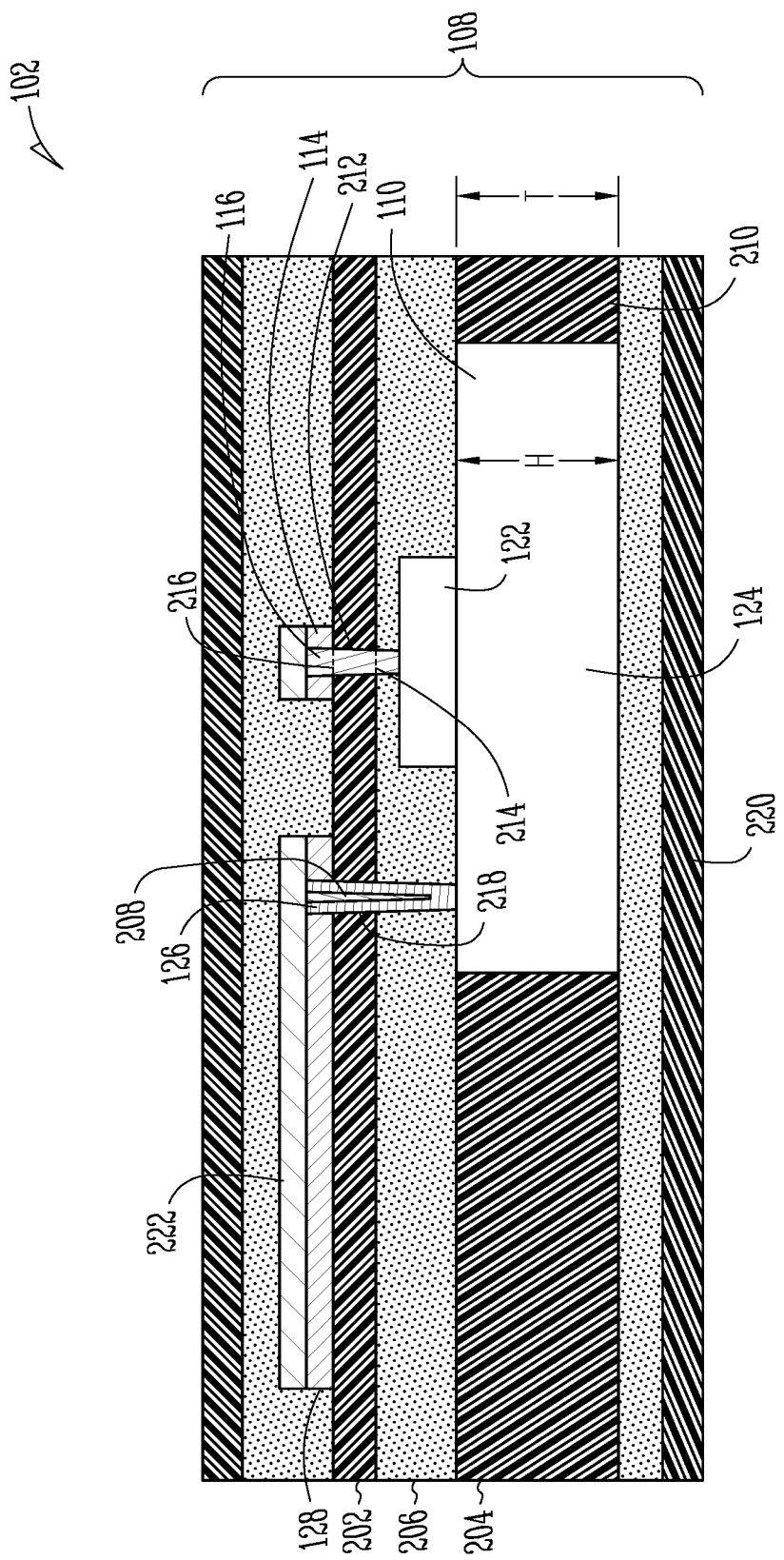
FIG. 2 illustrates a cross section of an example of a flexible circuit buzzer apparatus, according to an embodiment.

FIG. 2 illustrates a cross section of an example of a flexible circuit buzzer apparatus, such as the buzzer apparatus 102, according to an embodiment. The flexible circuit, such as flexible circuit 108 can include a plurality of dielectric elements laminated together with an adhesive. In the example, of FIG. 2, the flexible circuit 108 can include a first dielectric layer 202 and a second dielectric layer 204. For instance, the various dielectric layers can be constructed from a material including, but not limited to, at least one of a polyimide, polyester, polyether ether ketone, aramid, liquid crystal polymer (LCP), epoxy, glass, glass fabric, prepreg, FR4, or the like. The first dielectric layer 202 can be disposed on, and attached to, the second dielectric layer 204 with the adhesive, such as the adhesive 206. Various adhesive layers can include, but are not limited to, at least one of an acrylic, epoxy, fluoropolymer, or other type of adhesive. In some examples, the adhesive layer can be pressure activated, thermally activated, chemically activated, light activated, or other. In further examples, the flexible circuit 108 can include a metal clad laminate, such as a copper clad laminate, or an adhesiveless laminate.

At least one conductive layer, such as the first conductive layer 114 or the second conductive layer 126 can be attached to at least one of the dielectric layers, such as the first dielectric layer 202. For instance, the conductive layer can be attached to the dielectric layer by a process including but not limited to, electroless deposition, vapor deposition, sputtered deposition, chemical deposition, solution cast, or other deposition process. In a further example, the conductive layer can be a foil, such as a cold rolled and annealed foil that can be attached to the dielectric layer with the adhesive. A material of the conductive layer can include, but is not limited to, copper, silver, tin, gold, or other conductive material for communicating electrical signals. In some examples, one or more of the dielectric layers of the flexible circuit 108 can include at least one conductive layer attached on a first side or a second side of the dielectric layer. The conductive layer can be etched to form one or more electrical circuits, solder pads, ground planes, or other features from the conductive layer.

The buzzer 110 can be located within the flexible circuit 108. For instance, in the example of FIG. 2, the second dielectric layer 204 can include an aperture 210. The buzzer 110 can be located within the aperture 210. In an example, a height of the buzzer H can be equal to or less than a thickness T of the second dielectric layer 204. A hole 212 can be located in the dielectric layer, such as the first dielectric layer 202, and the conductive layer, such as the first conductive layer 114. The hole can include a first opening 214 on a first side of the dielectric layer and a second opening 216 on a second, opposing side, of the dielectric layer. The hole 212 can be located adjacent to the buzzer 110. For instance, the first opening 214 can be located adjacent to the first contact 122 and the second opening 216 can be located adjacent to the conductive layers, such as the first conductive layer 114. In an example, the hole 212 can be tapered. For instance, the hole 212 can include a smaller dimension proximate to the first opening 214 and a larger dimension proximate to the second opening 216. In an example, the first hole 212 can be a via hole, such as a microvia hole having a dimension of 150 μm or less transverse to a longitudinal axis of the hole 212. In a further example, a second hole 218 can be formed in the first dielectric layer 202. The second hole 218 can be located adjacent to the second contact 124. In an example, the second hole 218 can be sized and shaped like the first hole 212. For instance, the second hole 218 can include the taper or similar dimensions.

A conductive via can be located in the hole of the dielectric layer. For instance, in the example of FIG. 2, the first conductive via 116 can be located within the first hole 212 and the second conductive via 126 can be located within the second hole 218. The conductive via can electrically couple the buzzer 110 to the controller circuit 106 through one or more conductive layers. For instance, the first conductive via 116 can be electrically coupled between the first contact 122 and the first conductive layer 114, or the second conductive via 126 can be electrically coupled between the second contact 124 and the second conductive layer 128. The conductive via includes a plated material including at least one of a chemically deposited, electroplated, electroless deposition, vapor deposited, evaporative deposited, or sputtered plating, or other solderless material. For instance, the conductive via can be formed (e.g., deposited) in the hole, such as hole 212 or 218, and on the conductive layer, such as conductive layer 114 or 128, when the buzzer is in situ. In an example, the conductive via can include a tapered geometry corresponding to the taper of the hole in the dielectric layer. For instance, the conductive via can be tapered between the first opening and the second opening of the hole. In a further example, the conductive via can be a high density interconnect via having a dimension of 150 µm or less (e.g., as measured transverse to a longitudinal axis (e.g., diameter) of the hole).

The conductive via can be constructed of a material including, but not limited to, electroless copper, electrodeposited copper, shadow graphite or the like. In an example, the conductive via can include a thin film. For instance, the conductive via can be a thin film disposed on the conductive layer, the hole, and the contact. The thickness of the thin film can be less than the dimension of the hole (as measured transverse to a longitudinal direction of the hole (e.g., diameter)). Accordingly, the conductive via can include a cavity 208. In various examples, the cavity 208 can be filled, for instance, with materials including, but not limited to, electroplated copper, electroplated silver, electroplated gold, electroplated tin, epoxy, a polymer, a conductive polymer, shadow graphite, or the like. In a further example, the conductive via can include forming a substantially planar surface along the conductive layer and over the second opening, such as second opening 216.

In an example, a metallic coating, such as a thin metallic film, can be disposed between the conductive via (e.g., first conductive via 116 or second conductive via 126) and the hole (e.g., hole 212 or 218) or the conductive via and the first contact. The metallic coating can facilitate intermetallic adhesion between the conductive via and the contact, such as the first contact 122 or the second contact 124. In other words, the metallic coating can be metallurgically compatible with the conductive via to form an intermetallic bond between the metallic coating and the conductive via. For instance, the metallic coating can include a sputtered copper film or a silver plating. In an example, the metallic coating can be applied to the hole and the contact before the conductive via is applied. For instance, the metallic coating can be deposited in the hole and on the first contact when the buzzer 110 is in situ prior to depositing (e.g., plating) the conductive via. In a further example, a conductive plating 222 can be disposed on the conductive layer, such as the conductive layer 114 or 128, or on the conductive via. For instance, the conductive plating can be applied to increase the thickness of the conductive layer or the conductive via. In an example, the conductive plating can be applied by electroplating. The conductive plating can include, but is not limited to, a material including copper, nickel, silver, tin, lead, gold, or the like.

In the example of FIG. 2, the buzzer apparatus 102 can include a third dielectric layer, such as dielectric layer 220. The third dielectric layer 220 can be located on a side of the second dielectric layer 204 opposing the first dielectric layer 202. In an example, the buzzer 110 can be electrically isolated from a surrounding environment, such as the housing 104 or other component of the medical device 100.

Figure 3:
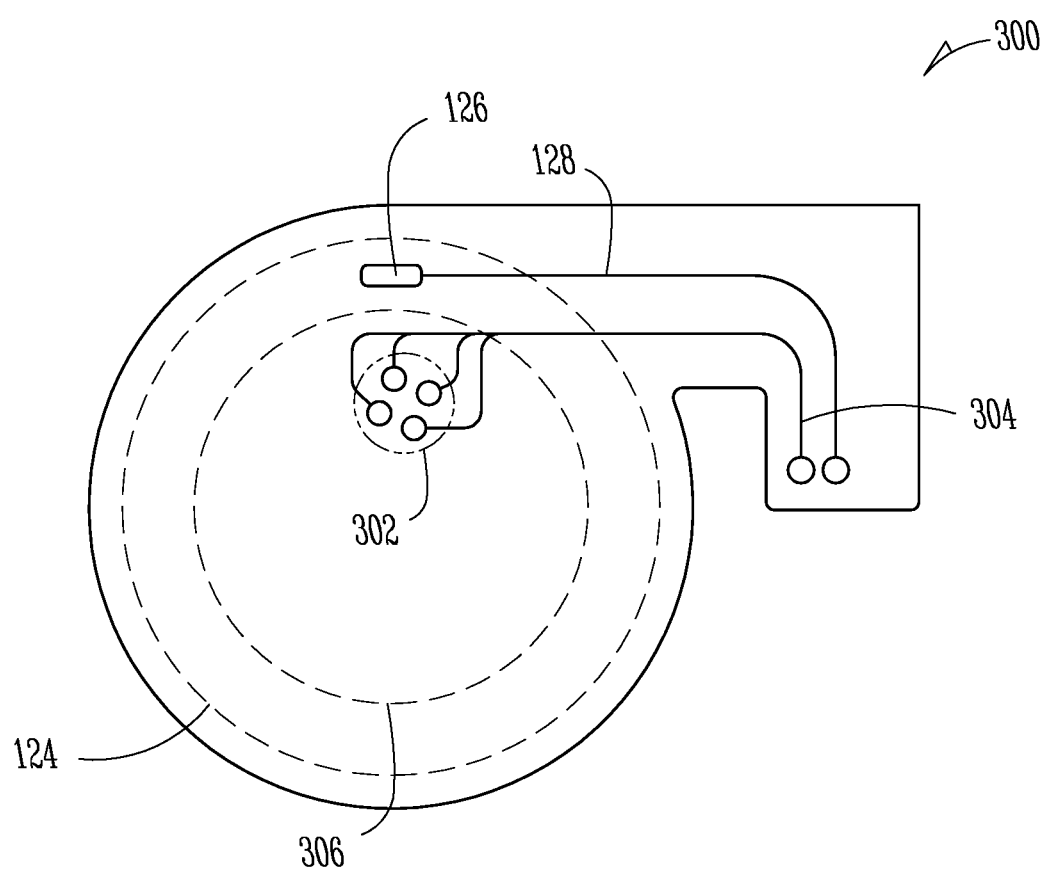
FIG. 3 illustrates a top view of an example of a flexible circuit buzzer apparatus including a group of conductive vias, according to an embodiment.

FIG. 3 illustrates a top view of an example of a flexible circuit buzzer apparatus, such as a buzzer apparatus 300 including a group of conductive vias 302, according to an embodiment. As shown in the example of FIG. 3, the group of conductive vias 302 can be electrically coupled between the conductive layer, such as conductive layer 304, and the first contact, such as the first contact 306. The group of conductive vias 302, can include, but is not limited to, two, three, four, five, or other number of conductive vias. In various examples, the group of conductive vias 302 can provide additional pathways for electrical signal transmission and additional mechanical joints for structural robustness as compared to a single conductive via, such as the conductive via 116. In other words, the group of conductive vias 302 can provide redundancy to the electrical coupling between the conductive layer and the contact. In an example, the group of electrically conductive vias 302 can include a spacing between two or more conductive vias of the group, the spacing being less than 0.20, 0.40, 0.60, 1.0, 2.0 mm, or other. For instance, the spacing can be 0.40 mm or less to reduce vibration dampening of the buzzer 110. In a further example, other conductive vias, such as the second conductive via 126, can be a group of conductive vias electrically coupled from the second conductive layer 128 to the second contact, such as the second contact 124.

Figure 4:
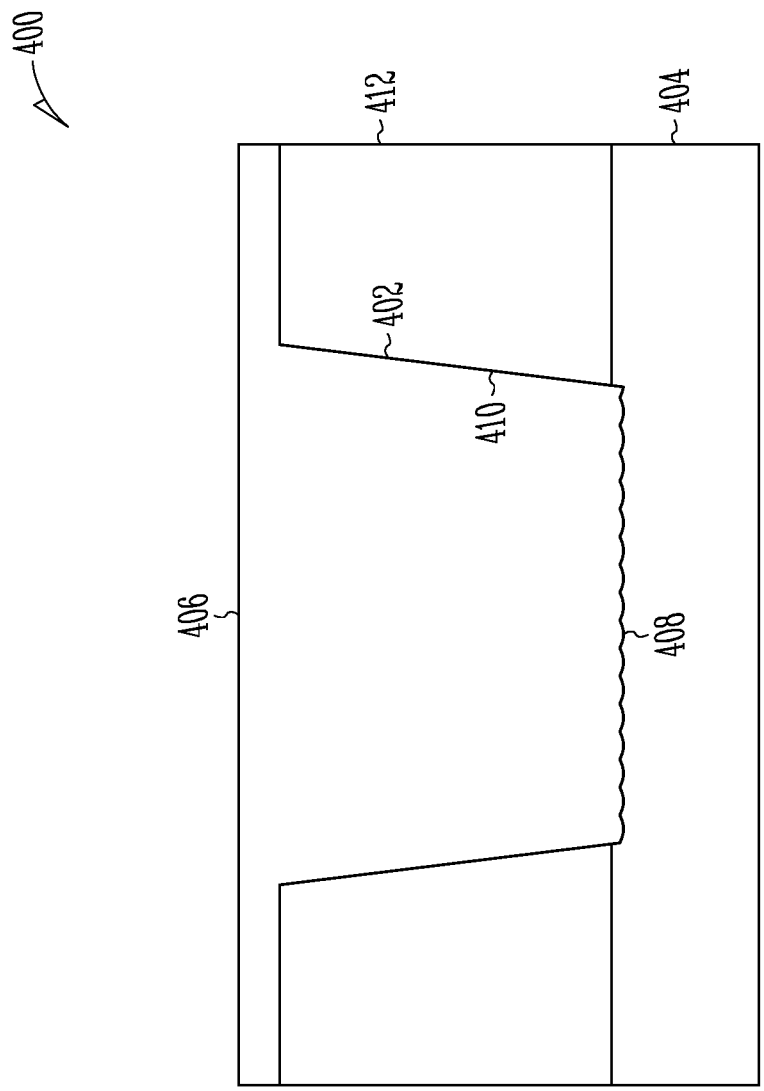
FIG. 4 illustrates a detailed cross section view of a conductive via, according to an embodiment.

FIG. 4 illustrates a detailed cross section view of a conductive via, such as conductive via 402, according to an embodiment. The conductive via 402 can electrically couple a conductive layer 406 (e.g., conductive layer 114) with a contact 404 (e.g., first contact 122). In the example of FIG. 4, the contact 404 can include a surface texture 408. The surface texture 408 can be located within the first opening (e.g., the first opening 214) of a hole 410 (such as hole 212 as previously described). In an example, the surface texture 408 can be formed by exposure to a laser. For instance, when the hole 410 is laser drilled into a dielectric layer 412 (e.g., dielectric layer 202 as previously described), the laser can ablate the contact 404 after the laser has removed the portion of the dielectric layer 412 proximate to the contact 404. In further examples, the surface texture 408 can be created by chemical etching, abrasion, or other methods of producing texture on the contact 404. In some examples, the surface texture 408 can include a surface roughness (e.g., peak to swell depth) between 1 nm to 10 µm. The conductive via 402 can be disposed (e.g., plated) on the surface texture 408. Accordingly, the conductive via 402 can fill or partially fill the pits (e.g., swells) of the surface texture 408. The surface texture 408 can be intertwined with the conductive via 402 to mechanically and electrically couple the conductive via 402 to the contact 404. For instance, the surface texture 408 can increase the strength of adhesion between the conductive via 402 and the contact 404.

Figure 5:
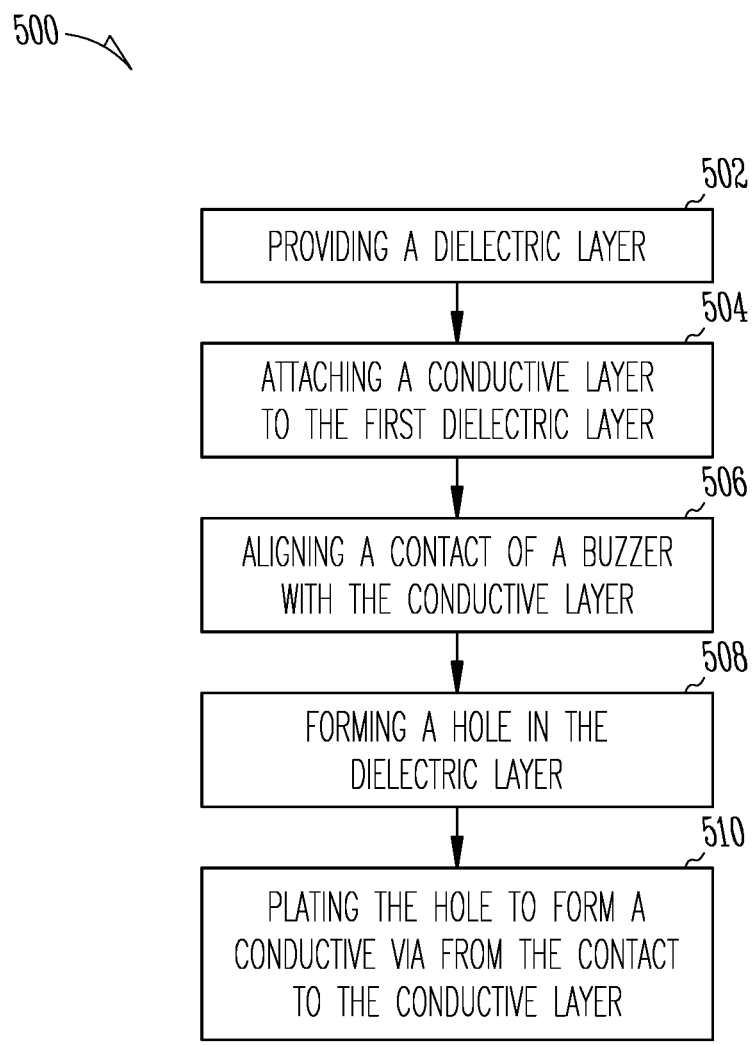
FIG. 5 illustrates an example of a method of making a flexible circuit buzzer apparatus, according to an embodiment.

FIG. 5 illustrates an example of a method 500 of making a flexible circuit buzzer apparatus, such as a buzzer apparatus 102 for use in the medical device 100, previously described in the examples herein and shown for instance in FIGS. 1-4. In describing the method 500, reference is made to one or more components, features, functions, and processes previously described herein. Where convenient, reference is made to the components, features, processes and the like with reference numerals. Reference numerals provided are exemplary and are nonexclusive. For instance, features, components, functions, processes, and the like described in the method 500 include, but are not limited to, the corresponding numbered elements provided herein. Other corresponding features described herein (both numbered and unnumbered) as well as their equivalents are also considered.

At 502, a dielectric layer can be provided. The dielectric layer can include, the first dielectric layer 202 as previously described herein. For instance, the dielectric layer can include a polyimide sheet. In an example, the polyimide sheet can have a thickness between 5 μm and 300 μm.

At 504, a conductive layer can be attached to the first dielectric layer. The conductive layer can include, the first conductive layer 114 or second conductive layer 128, as previously described herein. In an example, the conductive layer can be attached to the dielectric layer by electroless plating, chemical deposition, vapor deposition, evaporative deposition, adhesive bonding, thermal bonding, pressure, bonding, or other process of attaching the conductive layer.

At 506, a contact of a buzzer can be aligned with the conductive layer. In an example, the buzzer can include the buzzer 110 as previously described. The buzzer can be positioned adjacent to the dielectric layer. For instance, in an example, a first contact (e.g., first contact 122) can be aligned with the conductive layer (e.g., the first conductive layer 114). In a further example, a second contact (e.g., second contact 124) can be aligned with a second conductive layer (e.g., second conductive layer 128). The second conductive layer can be attached to the dielectric layer, such as on the same side of the dielectric layer as the first conductive layer. In an example, the buzzer can be attached to an adhesive layer (such as adhesive layer 206) located between the dielectric layer and the buzzer. For instance, the adhesive layer can attach the buzzer to the dielectric layer. In a further example, the adhesive can attach a second dielectric layer, such as dielectric layer 204, to the dielectric layer (e.g., first dielectric layer 202). The buzzer can be located in the second dielectric layer. For instance, an aperture can be cut in the second dielectric layer and the buzzer can be located in the aperture. The aperture can be formed by a die cutting, laser cutting, water jet cutting, machining, drilling, or other process.

At 508, a hole, such as hole 212, can be formed in the dielectric layer. The hole can include a first opening (e.g., first opening 214) and a second opening (e.g., second opening 216). The first opening can be located adjacent to a contact of the buzzer, such as the first contact 122 or second contact 124. In an example, the hole can include a dimension of 150 μm or less, such as a dimension transverse to a longitudinal axis of the hole (e.g., a diameter of the hole). The hole can be drilled, die cut, water jet drilled, laser drilled, or formed in the dielectric layer by another hole forming process. In an example, a surface texture, such as surface texture 408, can be formed on the contact (e.g., first contact 122 or second contact 124) of the buzzer. For instance, the surface texture can be formed by a laser. The laser can form the hole by removing material from the dielectric layer. In an example, the laser can dimple a surface of the contact after the dielectric layer is removed over the contact and accordingly produce the surface texture on the contact. In various examples, a second hole, such as second hole 218, or a group of holes, such as group 302, can be formed (e.g., drilled) into the dielectric layer as previously described herein. For instance, the second hole can be aligned with the second contact.

At 510, the hole can be plated to form a conductive via, such as a first conductive via 116 or a second conductive via 126, located from the contact to the conductive layer. For instance, the hole and the contact can be plated to form the conductive via electrically coupled between the conductive layer and the contact. In various examples, plating the hole, plating the first contact, or plating the conductive layer can include, but is not limited to, at least one of an electroplating, vapor deposition, chemically deposition, or sputtering process. For instance, the conductive via can be plated by electroless copper deposition into the hole. In a further example, the conductive via can be formed by filling the hole with shadow graphite or another solderless conductive material that can be deposited without the use of heat to melt the conductive material.

As previously described, a thin film or metallic coating, such as a thin film of copper can be deposited in the hole on at least the first contact or the conductive layer prior to forming the first conductive via. In a further example, the thin film or metallic coating can be deposited when the buzzer is in situ. In an example, the metallic coating can be metallurgically compatible with the conductive via. For instance, the first contact or second contact of the buzzer can be plated before alignment with the dielectric layer or in situ. In various examples, the metallic coating can be applied by one or more processes including, but not limited to, sputtering, electroplating, electroless plating, chemical deposition, vapor deposition, evaporative deposition, or other process as previously described herein. For instance, the metallic coating can include a silver plating or an electroless copper plating, or other sputtered thin film. Accordingly, an intermetallic bond between the metallic coating and the conductive via can be increased. In another example, where the contact includes the surface texture, such as the surface texture 408, the conductive via can be plated into the surface texture of the contact to mechanically couple the conductive layer to the contact. In an example, the conductive via can include a cavity. For instance, the conductive via can include a layer of conductive material plated or deposited on a side wall of the hole (e.g., bore). The thickness of the conductive via can be less than the dimension of the hole. As a result, the cavity can be located within the conductive via between the first opening and the second opening of the hole. In an example, the cavity can be filled. For instance, the cavity can be electroplated, filled with epoxy (e.g., conductive or non-conductive), or filled by another method. In a further example, the conductive via can be filled to form a substantially planar surface along the conductive layer and the second opening. Accordingly, a planar surface for attaching (e.g., laminating) another layer, such as a dielectric layer, adhesive layer, or conductive layer can be provided.

In an example, the second hole or the group of holes can be plated to form a second conductive via or group of conductive vias. For instance, the second conductive via or group of conductive vias can electrically couple the second contact to the second conductive layer.

Figure 6A:
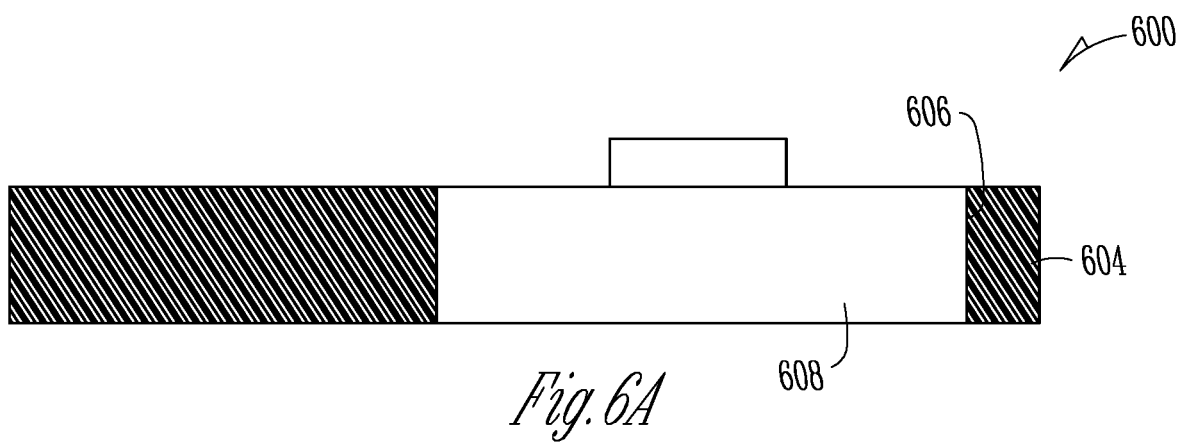
FIGS. 6A-F illustrate an example of a process of making a flexible circuit buzzer apparatus, according to an embodiment.
Figure 6B:
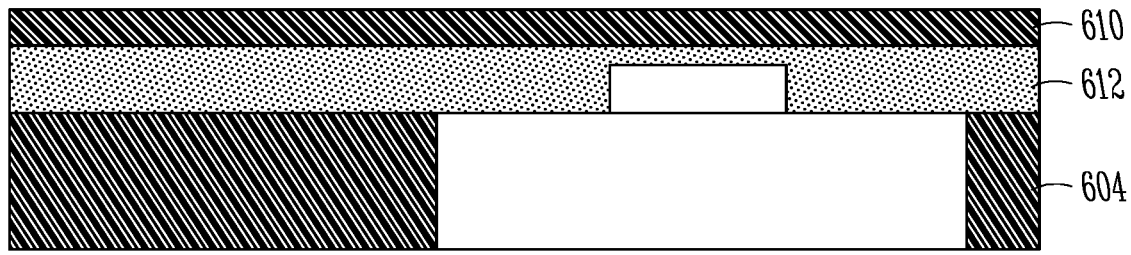

FIGS. 6A-F illustrate an example of a process 600 of making the flexible circuit buzzer apparatus, such as buzzer apparatus 602 (shown in the example of FIG. 6F), according to an embodiment. In the example of FIG. 6, a dielectric layer 604 can include an aperture 606. A buzzer 608 can be located within the aperture 606 as shown in FIG. 6A. In FIG. 6B a second dielectric layer, such as a dielectric layer 610 can be attached to the dielectric layer 604. For instance, the dielectric layer 610 can be attached to the dielectric layer 604 with an adhesive, such as adhesive 612.

Figure 6C:
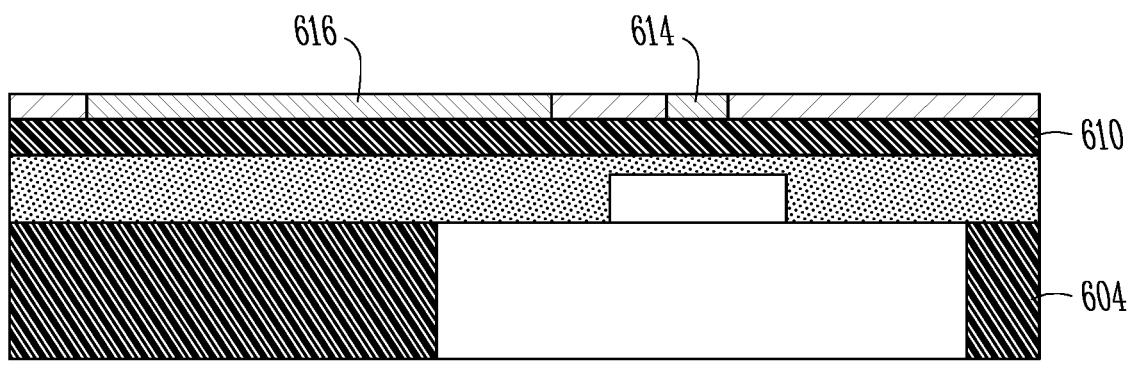

A conductive layer 614 can be attached to the dielectric layer 610 as shown in the example of FIG. 6C. For instance, the conductive layer 614 can be attached with adhesive or deposited (e.g., by electroless plating) as previously discussed. In a further example, a second conductive layer, such as conductive layer 616 can be attached to the dielectric layer 610. For instance, the conductive layer 614 and the conductive layer 616 can be configured as a first and a second electrical circuit respectively, such as a first and second electrical circuits for communicatively coupling to a controller circuit (e.g., the controller circuit 106 as shown in the example of FIG. 1 and described herein). The dielectric layer 604 can be a core material and the dielectric layer 610 and conductive layer 614 can be attached using a buildup process as used to construct a printed circuit board or a flexible printed circuit.

Figure 6D:
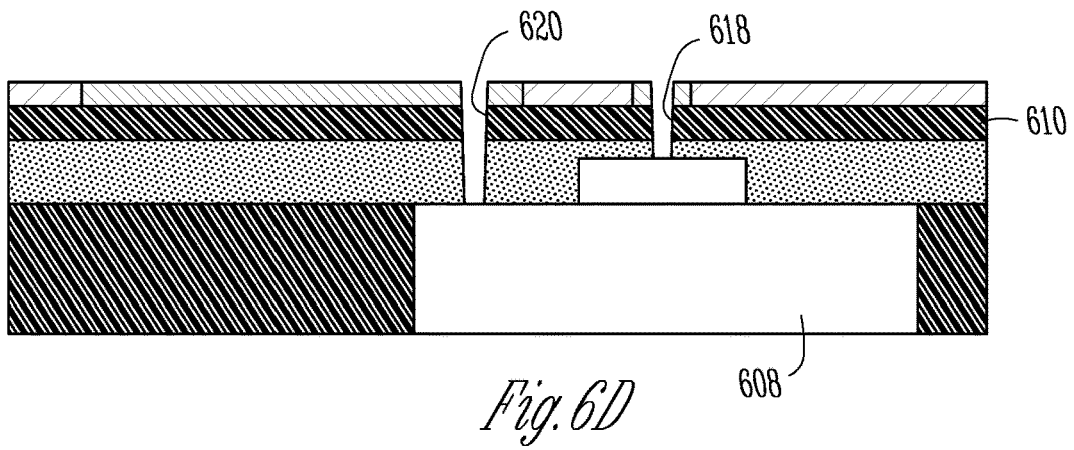

In the example of FIG. 6D, a hole 618 can be formed in the dielectric layer 610. For instance, the hole 618 can be mechanically drilled, laser drilled, or formed by other processes, such as those previously described. The hole 618 can be formed through the conductive layer 614 and extend to the buzzer 608. In an example, the hole 618 can extend to a contact of the buzzer 608, such as a first contact 122. In the example of FIG. 6D, a second hole, such as hole 620 can be formed in the dielectric layer 610. For instance, the hole 620 can be formed from the conductive layer 616 to the buzzer 608. As shown in the example, of FIG. 6D, the hole 620 can extend from the conductive layer 616 to a second contact of the buzzer 608, such as the second contact 124. Optionally, once the hole, such as hole 618 or 620, is drilled, a metallic coating can be deposited on the conductive layer (e.g., conductive layer 614 or conductive layer 616), the dielectric layer 610, the inner bore of the hole (e.g., hole 618 or hole 620), and on the buzzer 608 (e.g., on the first contact or the second contact). For instance, the metallic coating can be applied by sputtering or electroless platting to form a thin film. In an example, the metallic coating can increase adhesion between the buzzer 608 and later platings or depositions, such as the conductive via.

Figure 6E:
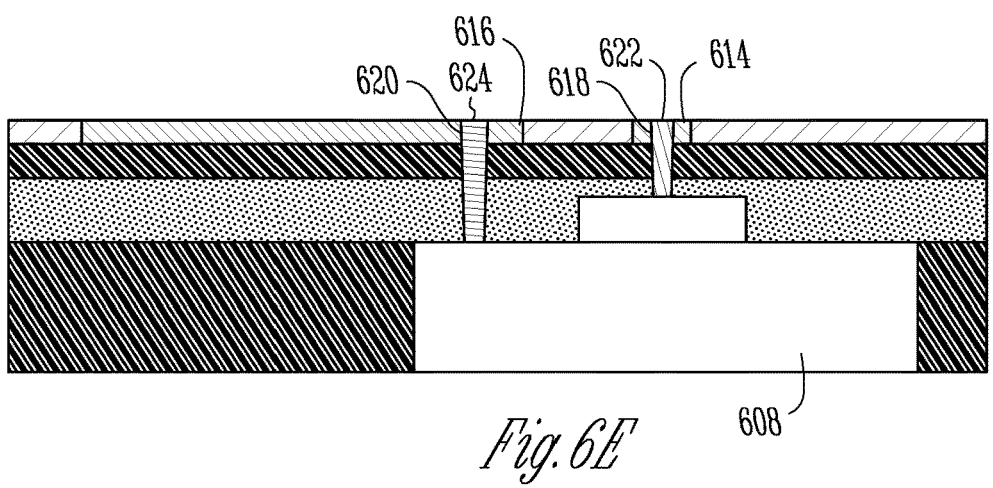

A conductive via 622 can be plated on to the inner bore of the hole 618 as shown in the example of FIG. 6E. For instance, the conductive via 622 can be plated on to the conductive layer 614, the inner bore of the hole 618, and the buzzer 608, such as on a first contact of the buzzer 608. In other words, the conductive via can be plated from the conductive layer 614 to the first contact to electrically couple the conductive layer 614 to the first contact. As shown in FIG. 6E, a second conductive via 624 can be plated on the inner bore of the hole 620. The second conductive via 624 can be plated on the conductive layer 616, the inner bore of the hole 620, and the buzzer 608, such as the second contact of the buzzer 608. The second conductive via 624 can electrically couple the conductive layer 616 to the second contact. Optionally, the conductive via can be plated on the metallic coating as previously described. In some examples, the metallic coating can improve intermetallic bonding between the conductive via and the buzzer 608. Where the conductive via includes a cavity, the cavity can be filled as previously discussed. For instance, the cavity can be filled with electroplated copper or a conductive adhesive in some examples.

Figure 6F:
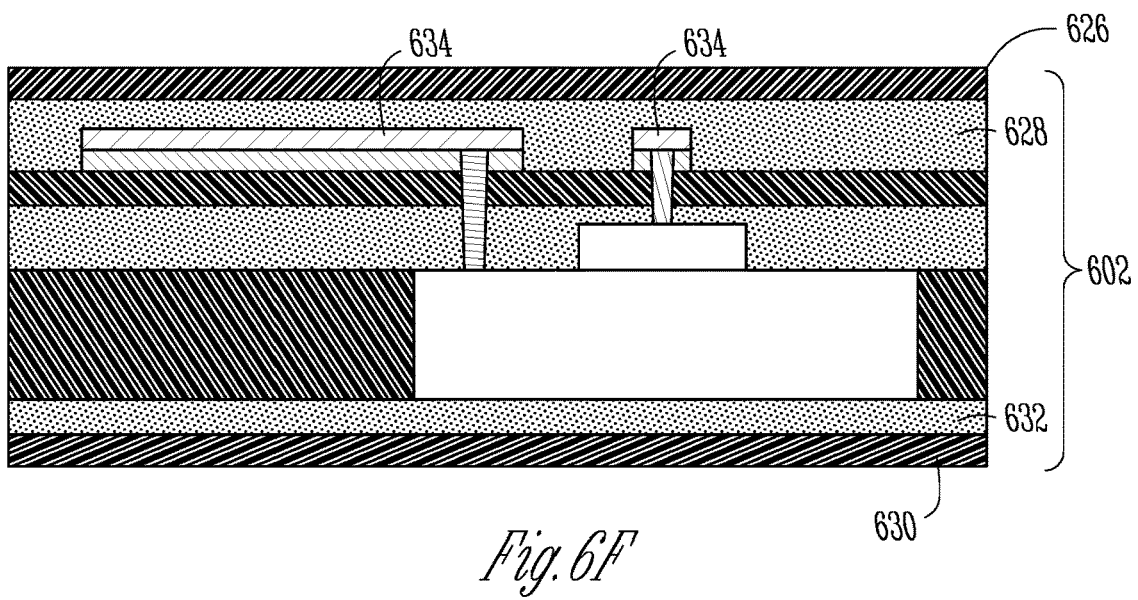

In the example shown in FIG. 6F, a dielectric layer 626 can be attached to one or more of the dielectric layer 610, the conductive layer 614, the conductive layer 616, the conductive via 622, or the conductive via 624 with an adhesive 628. A dielectric layer 630 can be attached to the dielectric layer 604 with an adhesive 632. Accordingly, the buzzer 608 can be electrically isolated from the external environment. In the example of FIG. 6F, a metallic coating 634 can be plated on the conductive layer 614 or the conductive layer 616. The metallic coating 634 can increase the thickness of the conductive layer, for instance, to decrease the electrical resistance of the conductive layer. In an example, the metallic coating 634 can be electroplated on to the conductive layer. In the example of FIG. 6F, the metallic coating 634 can include electroplated copper. Accordingly, the buzzer apparatus 602 can be constructed by the process 600.

Figure 7:
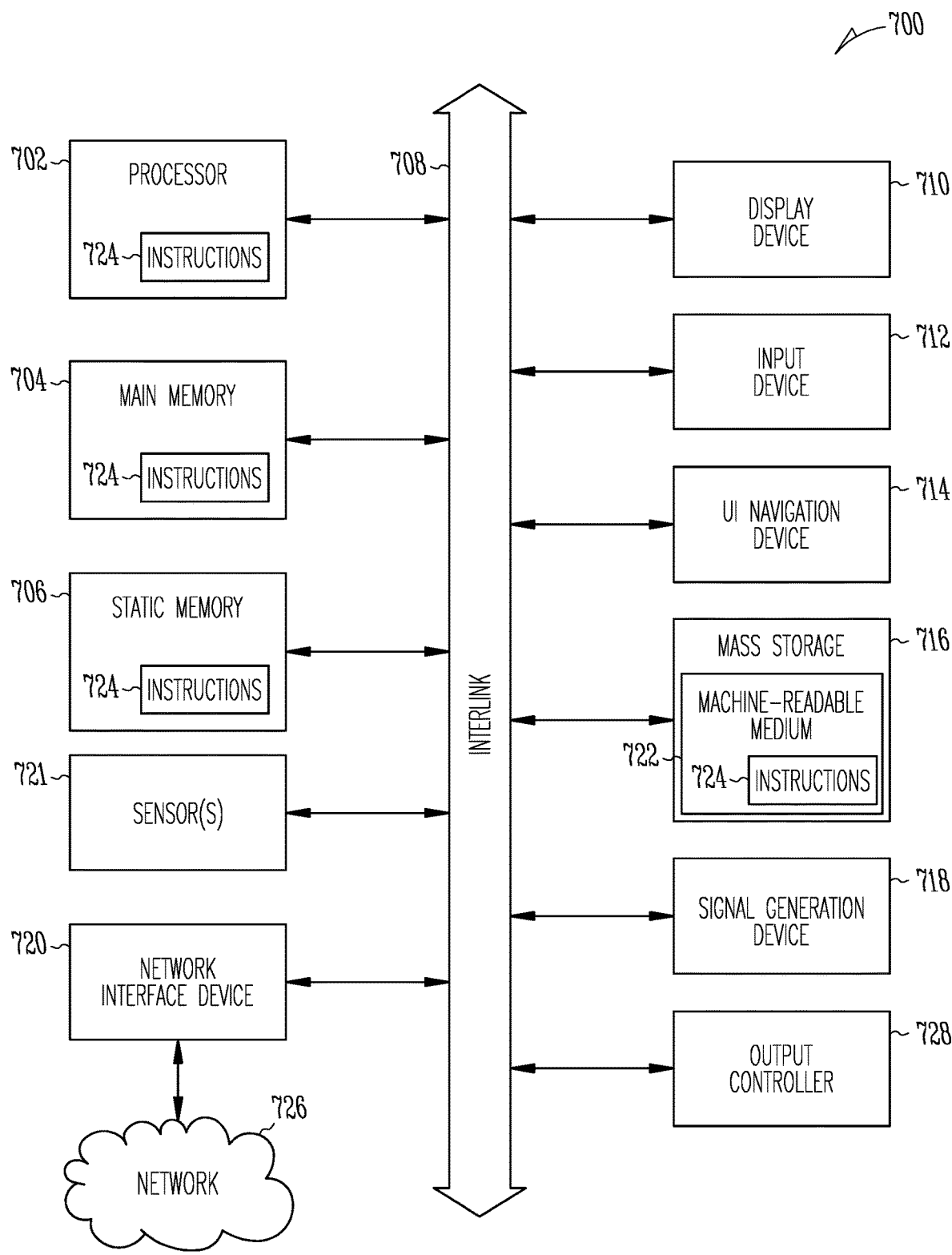
FIG. 7 illustrates a block diagram of an example machine upon which any one or more of the techniques (e.g., methodologies) discussed herein may perform.

FIG. 7 illustrates a block diagram of an example machine into which a piezoelectric buzzer may be integrated and upon which any one or more of the techniques (e.g., methodologies) discussed herein may perform. Portions of this description may apply to the computing framework of various portions of the implantable medical device, such as implantable medical device 102 or the external system, or an implantable device operating as part of a system. In alternative embodiments, the machine 700 may operate as a standalone device or may be connected (e.g., networked) to other machines. For example, in a networked deployment, the machine 700 may operate in the capacity of a server machine, a client machine, or both in server-client network environments. In some examples, portions of the machine such as stimulation therapy electrodes coupled to an output controller 728, may be part of or coupled to an implantable device, and other portions, such as a touchscreen input device, display device, or physical ports may be part of an external (non-implanted) system.

In an example, the machine 700 may act as a peer machine in peer-to-peer (P2P) (or other distributed) network environment. The machine 700 may be or include a special purpose implantable or wearable device, personal computer (PC), a tablet PC, a set-top box (STB), a personal digital assistant (PDA), a mobile telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein, such as cloud computing, software as a service (SaaS), other computer cluster configurations.

Examples, as described herein, may include, or may operate by, logic or a number of components, or mechanisms. Circuit sets are a collection of circuits implemented in tangible entities that include hardware (e.g., simple circuits, gates, logic, etc.). Circuit set membership may be flexible over time and underlying hardware variability. Circuit sets include members that may, alone or in combination, perform specified operations when operating. In an example, hardware of the circuit set may be immutably designed to carry out a specific operation (e.g., hardwired). In an example, the hardware of the circuit set may include variably connected physical components (e.g., execution units, transistors, simple circuits, etc.) including a computer readable medium physically modified (e.g., magnetically, electrically, moveable placement of invariant massed particles, etc.) to encode instructions of the specific operation. In connecting the physical components, the underlying electrical properties of a hardware constituent are changed, for example, from an insulator to a conductor or vice versa. The instructions enable embedded hardware (e.g., the execution units or a loading mechanism) to create members of the circuit set in hardware via the variable connections to carry out portions of the specific operation when in operation.

Accordingly, the computer readable medium is communicatively coupled to the other components of the circuit set member when the device is operating. In an example, any of the physical components may be used in more than one member of more than one circuit set. For example, under operation, execution units may be used in a first circuit of a first circuit set at one point in time and reused by a second circuit in the first circuit set, or by a third circuit in a second circuit set at a different time.

Machine (e.g., computer system) 700 may include a hardware processor 702 (e.g., a central processing unit (CPU), a graphics processing unit (GPU), a hardware processor core, or any combination thereof), a main memory 704 and a static memory 706, some or all of which may communicate with each other via an interlink (e.g., bus) 708. The machine 700 may further include a display unit 710 (e.g., a raster display, vector display, holographic display, etc.), an alphanumeric input device 712 (e.g., a keyboard), and a user interface (UI) navigation device 714 (e.g., a mouse). In an example, the display unit 710, input device 712 and UI navigation device 714 may be a touch screen display. The machine 700 may additionally include a storage device (e.g., drive unit) 716, a signal generation device 718 (e.g., a piezoelectric buzzer), a network interface device 720 such as a MICS or Bluetooth radio, and one or more sensors 721, such as an electrode capable of detecting cardiac signals (e.g., cardiac activation or depolarization), respiration, an acoustic sensor configured to detect heart sounds, or other physiologic signals, a global positioning system (GPS) sensor, compass, accelerometer, or other sensor. The machine 700 may include an output controller 728, such as a serial (e.g., universal serial bus (USB), parallel, or other wired or wireless (e.g., infrared (IR), near field communication (NFC), etc.) connection to communicate or control one or more peripheral devices (e.g., a printer, card reader, etc.).

The storage device 716 may include a machine readable medium 722 on which is stored one or more sets of data structures or instructions 724 (e.g., software) embodying or utilized by any one or more of the techniques or functions described herein. The instructions 724 may also reside, completely or at least partially, within the main memory 704, within static memory 706, or within the hardware processor 702 during execution thereof by the machine 700. In an example, one or any combination of the hardware processor 702, the main memory 704, the static memory 706, or the storage device 716 may constitute machine readable media.

While the machine readable medium 722 is illustrated as a single medium, the term "machine readable medium" may include a single medium or multiple media (e.g., a centralized or distributed database, and/or associated caches and servers) configured to store the one or more instructions 724.

The term "machine readable medium" may include any medium that is capable of storing, encoding, or carrying instructions for execution by the machine 700 and that cause the machine 700 to perform any one or more of the techniques of the present disclosure, or that is capable of storing, encoding or carrying data structures used by or associated with such instructions. Non-limiting machine readable medium examples may include solid-state memories, and optical and magnetic media. In an example, a massed machine readable medium includes a machine readable medium with a plurality of particles having invariant (e.g., rest) mass. Accordingly, massed machine-readable media are not transitory propagating signals. Specific examples of massed machine readable media may include: non-volatile memory, such as semiconductor memory devices (e.g., Electrically Programmable Read-Only Memory (EPROM), Electrically Erasable Programmable Read-Only Memory (EEPROM)) and flash memory devices; magnetic disks, such as internal hard disks and removable disks; magneto-optical disks; and CD-ROM and DVD-ROM disks.

The instructions 724 may further be transmitted or received over a communications network 726 using a transmission medium via the network interface device 720 utilizing any one of a number of transfer protocols (e.g., frame relay, internet protocol (IP), transmission control protocol (TCP), user datagram protocol (UDP), hypertext transfer protocol (HTTP), etc.). Example communication networks may include a local area network (LAN), a wide area network (WAN), a packet data network (e.g., the Internet), mobile telephone networks (e.g., cellular networks), Plain Old Telephone (POTS) networks, and wireless data networks (e.g., Institute of Electrical and Electronics Engineers (IEEE) 802.11 family of standards known as WiFi®, IEEE 802.16 family of standards known as WiMax®), IEEE 802.15.4 family of standards, peer-to-peer (P2P) networks, among others. In an example, the network interface device 720 may include one or more physical jacks (e.g., Ethernet, coaxial, or phone jacks) or one or more antennas to connect to the communications network 726. In an example, the network interface device 720 may include a plurality of antennas to wirelessly communicate using at least one of single-input multiple-output (SIMO), multiple-input multiple-output (MIMO), or multiple-input single-output (MISO) techniques. The term "transmission medium" shall be taken to include any intangible medium that is capable of storing, encoding or carrying instructions for execution by the machine 700, and includes digital or analog communications signals or other intangible medium to facilitate communication of such software.

Various embodiments are illustrated in the figures above. One or more features from one or more of these embodiments may be combined to form other embodiments.

Method examples described herein can be machine or computer-implemented at least in part. Some examples may include a computer-readable medium or machine-readable medium encoded with instructions operable to configure an electronic device or system to perform methods as described in the above examples. An implementation of such methods can include code, such as microcode, assembly language code, a higher-level language code, or the like. Such code can include computer readable instructions for performing various methods. The code can form portions of computer program products. Further, the code can be tangibly stored on one or more volatile or non-volatile computer-readable media during execution or at other times.

The above detailed description is intended to be illustrative, and not restrictive. The scope of the disclosure should, therefore, be determined with references to the appended claims, along with the full scope of equivalents to which such claims are entitled.

What is claimed is:

1. A flexible circuit buzzer apparatus for use in an implantable medical device, comprising:
   a flexible circuit having a first dielectric layer;
   a conductive layer disposed on the first dielectric layer;
   a hole in the first dielectric layer;
   a buzzer including a first contact located proximate to the hole; and
   a conductive via in the hole, wherein at least the first contact is electrically coupled to the conductive layer by the conductive via.

2. The apparatus of claim 1, wherein the buzzer is located within an aperture of a second dielectric layer, the second dielectric layer is coupled to the first dielectric layer.

3. The apparatus of claim 1, further comprising a group of redundant conductive vias electrically coupled between the conductive layer and the first contact, a spacing between two or more conductive vias of the group being less than 0.40 mm.

4. The apparatus of claim 1, wherein the conductive via is a high density interconnect via having a dimension of 150 μm or less transverse to a longitudinal axis of the hole.

5. The apparatus of claim 1, wherein the conductive via includes a plated material selected from at least one of a group comprising a chemically deposited, electroplated, electroless deposition, vapor deposited, evaporative deposited, and sputtered plating.

6. The apparatus of claim 1, wherein the conductive via includes electroless copper, electro-deposited copper, or shadow graphite.

7. The apparatus of claim 1, wherein the hole includes a first opening on a first side of the first dielectric layer and a second opening on a second side of the dielectric layer, the first opening being proximate the first contact and the second opening being proximate the conductive layer, and wherein the conductive via is tapered, the conductive via having a smaller dimension proximate to the first opening than proximate to the second opening.

8. A system, comprising:
   a flexible circuit buzzer apparatus for use in an implantable medical device, the buzzer apparatus including:
      a flexible circuit,
      a buzzer laminated into the flexible circuit,
      a conductive via in the flexible circuit; and
      wherein the buzzer is operatively coupled to a controller circuit in a housing of the implantable medical device through the via.

9. The system of claim 8, wherein the flexible circuit includes a first dielectric layer including a first hole extending through the first dielectric layer, a first conductive layer disposed on the first dielectric layer, a buzzer including a first contact located proximate to the first hole; and the conductive via in the first hole, the first contact being electrically coupled to the first conductive layer by the conductive via, and the first conductive layer being coupled to the controller circuit.

10. The system of claim 9, further comprising a second dielectric layer, the buzzer being between the first dielectric layer and the second dielectric layer, wherein the buzzer is electrically isolated from a surrounding environment.

11. The system of claim 9, wherein the flexible circuit further comprises a second hole extending through the first dielectric layer, and a second conductive via in the second hole, the second conductive via being electrically coupled to the first conductive layer.

12. The system of claim 11, wherein the flexible circuit further comprises a third hole extending through the first dielectric layer, and a third conductive via in the third hole, the third conductive via being coupled to a ground connection.

13. The system of claim 9, wherein the buzzer has a central region and a peripheral region, and the first via is located at a peripheral region of the buzzer.

14. The system of claim 8, comprising the implantable medical device, the implantable medical device comprising the housing, the controller circuit, and the flexible circuit buzzer apparatus.

* * * * *